United States Patent
Gatenholm et al.

(10) Patent No.: US 8,691,974 B2
(45) Date of Patent: Apr. 8, 2014

(54) THREE-DIMENSIONAL BIOPRINTING OF BIOSYNTHETIC CELLULOSE (BC) IMPLANTS AND SCAFFOLDS FOR TISSUE ENGINEERING

(75) Inventors: Paul Gatenholm, Blacksburg, VA (US); Henrik Backdahl, Goteburg (SE); Theodore Jon Tzavaras, Virginia Beach, VA (US); Rafael V. Davalos, Blacksburg, VA (US); Michael B. Sano, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 8 days.

(21) Appl. No.: 13/498,657

(22) PCT Filed: Sep. 28, 2010

(86) PCT No.: PCT/US2010/050460
§ 371 (c)(1),
(2), (4) Date: Mar. 28, 2012

(87) PCT Pub. No.: WO2011/038373
PCT Pub. Date: Mar. 31, 2011

(65) Prior Publication Data
US 2012/0190078 A1 Jul. 26, 2012

Related U.S. Application Data

(60) Provisional application No. 61/246,210, filed on Sep. 28, 2009.

(51) Int. Cl.
*C08B 1/00* (2006.01)
*A61K 31/717* (2006.01)
*C12P 1/04* (2006.01)
*C12N 11/12* (2006.01)

(52) U.S. Cl.
USPC ............... 536/56; 536/124; 514/57; 435/170; 435/179

(58) Field of Classification Search
USPC ................ 536/56, 124; 514/57; 435/170, 179
See application file for complete search history.

(56) References Cited

U.S. PATENT DOCUMENTS

| | | |
|---|---|---|
| 5,228,900 A | 7/1993 | Stephens et al. |
| 5,871,978 A | 2/1999 | Ben-Bassat et al. |
| 5,885,829 A | 3/1999 | Mooney et al. |
| 6,143,293 A | 11/2000 | Weiss et al. |
| 6,197,575 B1 | 3/2001 | Griffith et al. |
| 2001/0043949 A1 | 11/2001 | Delgado |
| 2002/0143403 A1 | 10/2002 | Vaidyanathan et al. |
| 2002/0182241 A1 | 12/2002 | Borenstein et al. |
| 2004/0096509 A1 | 5/2004 | Hutchens et al. |
| 2006/0182941 A1 | 8/2006 | Yano et al. |

FOREIGN PATENT DOCUMENTS

| | | |
|---|---|---|
| EP | 0228779 A | 7/1987 |
| JP | 2008127510 | 6/2008 |
| JP | 2008127510 A | 6/2008 |
| JP | 2009007721 | 1/2009 |
| JP | 2009007721 A | 1/2009 |
| WO | 0161026 A | 8/2001 |
| WO | 2006042287 A | 4/2006 |
| WO | 2008040729 A | 4/2008 |
| WO | 2011038373 A | 3/2011 |

OTHER PUBLICATIONS

International Preliminary Report on Patentability, Apr. 3, 2012, PCT/US10/50460.
International Search Report and Written Opinion, Jun. 23, 2011, PCT/US10/50460.

*Primary Examiner* — Eric S Olson
*Assistant Examiner* — Michael C Henry
(74) *Attorney, Agent, or Firm* — Whitham Curtis Christofferson & Cook, PC

(57) ABSTRACT

A novel BC fermentation technique for controlling 3D shape, thickness and architecture of the entangled cellulose nanofibril network is presented. The resultant nano-cellulose based structures are useful as biomedical implants and devices, are useful for tissue engineering and regenerative medicine, and for health care products. More particularly, embodiments of the present invention relate to systems and methods for the production and control of 3-D architecture and morphology of nano-cellulose biomaterials produced by bacteria using any biofabrication process, including the novel 3-D Bioprinting processes disclosed. Representative processes according to the invention involve control of the rate of production of biomaterial by bacteria achieved by meticulous control of the addition of fermentation media using a microfluidic system. In exemplary embodiments, the bacteria gradually grew up along the printed alginate structure that had been placed into the culture, incorporating it. After culture, the printed alginate structure was successfully removed revealing porosity where the alginate had been placed. Porosity and interconnectivity of pores in the resultant 3-D architecture can be achieved by porogen introduction using, e.g., ink-jet printer technology.

8 Claims, 5 Drawing Sheets

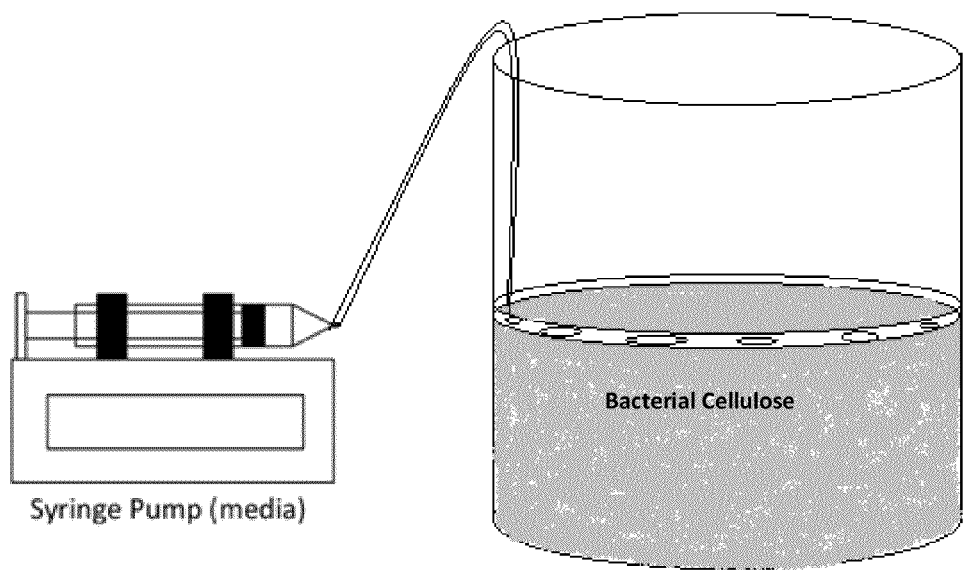
FIG. 1
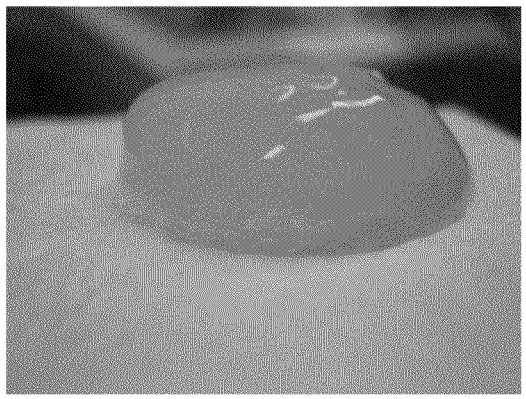      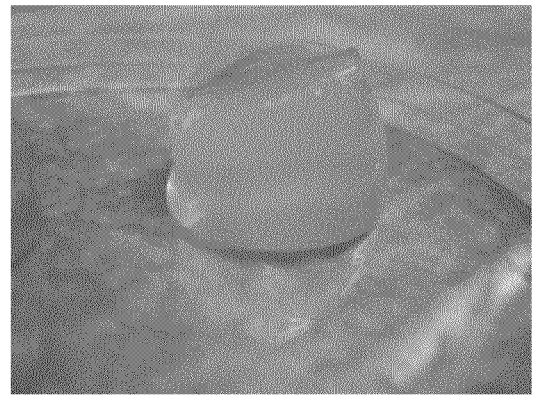
FIG. 2A      FIG. 2B

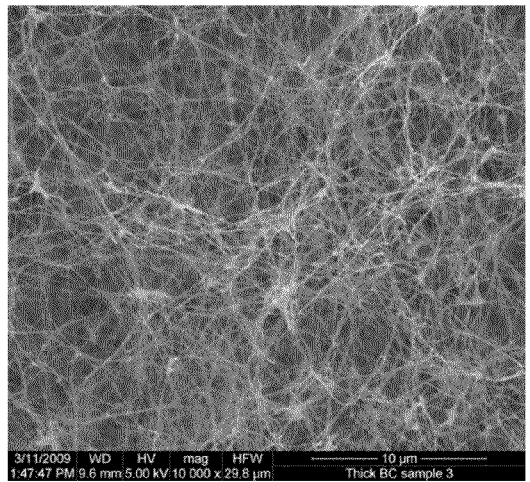
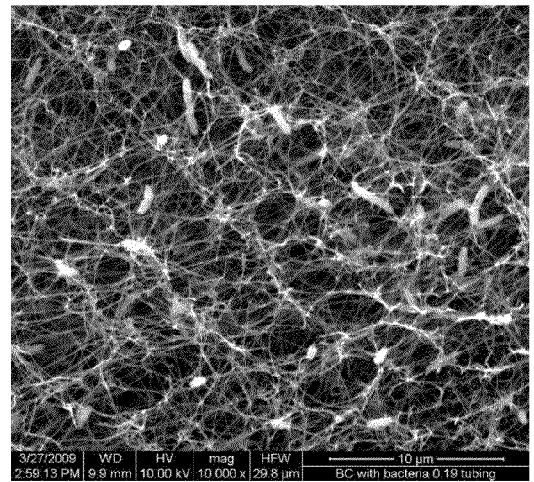
FIG. 5A            FIG. 5B
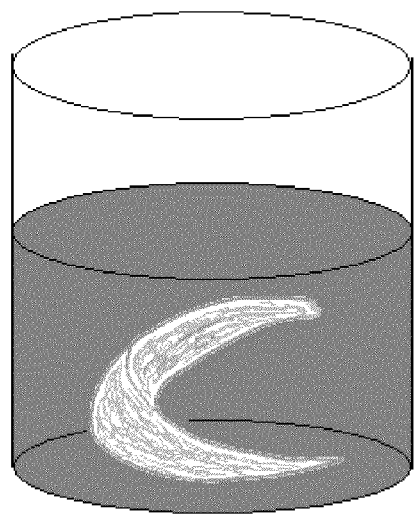
FIG. 6

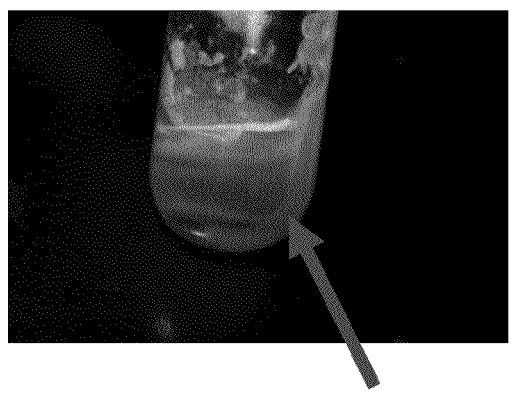
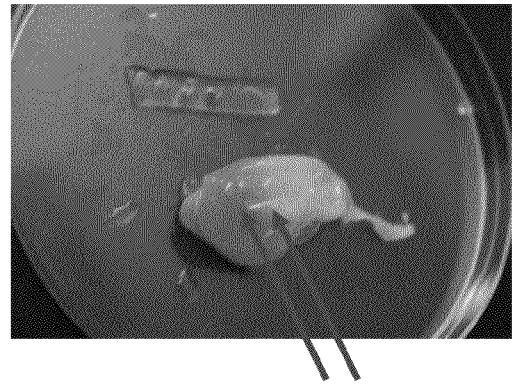
FIG. 7A          FIG. 7B
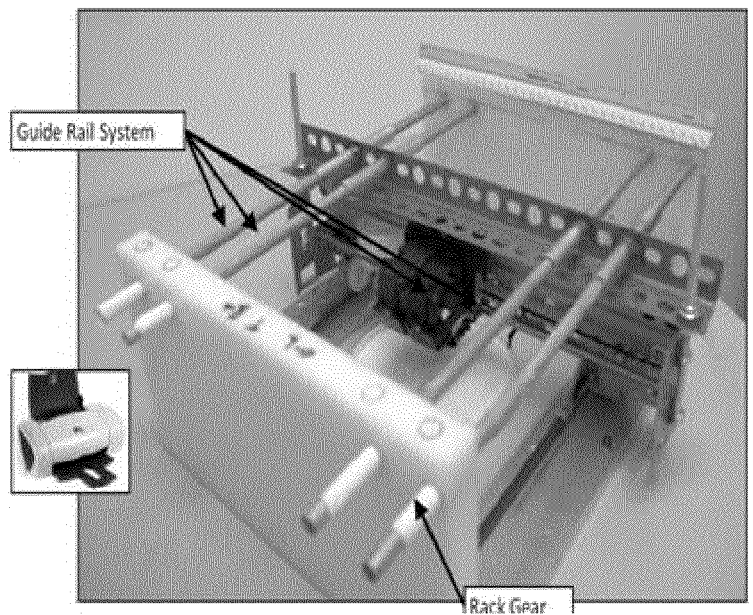
FIG. 8

THREE-DIMENSIONAL BIOPRINTING OF BIOSYNTHETIC CELLULOSE (BC) IMPLANTS AND SCAFFOLDS FOR TISSUE ENGINEERING

CROSS-REFERENCE TO RELATED APPLICATION

This application is a U.S. National Stage application of International Application No. PCT/US10/50460, filed Sep. 28, 2010, which application relies on the disclosure of and claims priority to U.S. Provisional Patent Application No. 61/246,210 filed on Sep. 28, 2009, the disclosure of which is incorporated by reference herein in its entirety.

BACKGROUND OF THE INVENTION

1. Field of the Invention

The present invention relates to biomedical implants and devices, tissue engineering and regenerative medicine, and health care products. More particularly, embodiments of the present invention relate to systems and methods for production and control of 3-D architecture and morphology of nanocellulose biomaterials produced by bacteria using novel biofabrication processes, such as 3-D Bioprinting. Representative processes according to the invention involve control of the rate of production of biomaterial by bacteria achieved by meticulous control of addition of fermentation media using a microfluidic system. If desired, porosity and interconnectivity of pores within the resultant 3-D architecture can be achieved by porogen introduction using, for example, ink-jet printer technology.

2. Description of the Related Art

Tissue engineering and regenerative medicine provide the revolutionary solution for tissue and organ replacement. Millions of patients suffer today from lack of organ due to trauma or loss of organ due to disease such as cancer followed by surgery. Increased elder population is of need of worn tissue and organs in order to be able to live a comfortable life. Synthetic materials have only had limited success as implants due to a lack of biocompatibility and mismatch of biomechanical performance. Natural polymers are much better suited as biomaterials due to generally better biocompatibility and improved tissue integration. Tissue engineering is based on the use of scaffold materials with very well defined morphology to host the cells and provide support for cell producing extracellular matrix. The major bottle-neck in the field of tissue engineering and regenerative medicine is a lack of scaffolds with tailor-made architecture which is caused by lack of production technology to control biomaterial's architecture in great detail.

Natural polymers such as collagen or elastin have been extensively evaluated as implants and scaffold for tissue engineering. The major drawback of these protein based materials is immunological response and difficulty to process these materials into porous scaffolds with predetermined morphology. Polysaccharides such as hyaluronic acid, alginates, chitosan and cellulose have been recently successfully introduced as scaffolds for tissue engineering. They can be easily sterilized and they do not cause immunological response. Cellulose ($\beta$-1→4-glucan) is a natural polysaccharide biosynthesized by a majority of plants. Cellulose is attractive as a biomaterial because of its good mechanical properties (Bäckdahl, H., Helenius, G., Bodin, A., Johansson, B., Nanmark, U., Risberg, B., and Gatenholm, P., Bacterial Cellulose as Potential Scaffold for Tissue Engineered Blood Vessels: Mechanical Properties and Cell Interactions, *Biomaterials*, 27, 2141-2149 (2006)), hydroexpansivity (Gelin, K., Bodin, A., Gatenholm, P., Mihranyan, A., Edwards, K and Strømme, M., Characterization of Water in Bacterial Cellulose Using Dielectric Spectroscopy and Electron Microscopy, *Polymer*, 48, 7623-7631 (2007)), biocompatibility (Gatenholm, P., and Klemm, D., Bacterial Nanocellulose as a Renewable Material for Biomedical Applications, *MRS Bulletin*, 35 (3), 208-213, 2010), and structural stability within a wide range of temperatures and pH levels. In addition to being synthesized in vast amounts as a structural material in the walls of plants, cellulose can also be produced as an exopolysaccharide, i.e. biosynthetic cellulose (BC) synthesized by bacteria such as *Acetobacter xylinum* (Gatenholm, P., and Klemm, D., Bacterial Nanocellulose as a Renewable Material for Biomedical Applications, *MRS Bulletin*, 35 (3), 208-213, (2010)).

BC has been recently evaluated in several biomedical applications. In addition to being used for microsurgery (Gatenholm, P., and Klemm, D., Bacterial Nanocellulose as a Renewable Material for Biomedical Applications, *MRS Bulletin*, 35 (3), 208-213, (2010)), it has been evaluated as vascular grafts (Bäckdahl, H., Risberg, B., and Gatenholm, P., Observation on Bacterial Cellulose Tube Formation for Application as Vascular Graft, *Materials, Science and Engineering*, Part C in press 2010), cartilage replacement (Svensson, A., Nicklasson, E. Harrah, T., Panilaitis, B., Kaplan, D. Brittberg. M, and Gatenholm, P., Bacterial Cellulose as a Potential Scaffold for Tissue Engineering of Cartilage, *Biomaterials*, 26, 419-431 (2005)), bone grafts (Zaborowska, M., Bodin, A., Bäckdahl, H., Popp, J., Goldstein, A., and Gatenholm, P., Microporous Bacterial Cellulose as a Potential Scaffold for Bone Regeneration, *Acta Biomaterialia*, 6 (7), 2540-2547, 2010), and meniscus implant (Bodin, A., Concaro, S., Brittberg, M., and Gatenholm, P., Bacterial Cellulose as a Potential Meniscus Implant, *Journal of Tissue Engineering and Regenerative Medicine*, 48, 7623-7631 (2007)).

The high water content of biosynthetic cellulose, around 99%, makes it attractive to be used as a hydrogel, which is known for its favorable biocompatible properties and low protein adsorption. BC is a versatile material that can be manufactured in various sizes and shapes. The process of manufacturing is biotechnological process and requires detailed control of bacterial proliferation, migration and rate of production of cellulose. In a typical static culture there is, however, only very limited control of nano-cellulose production process.

Another of the challenges of using biosynthetic cellulose as a scaffold for tissue engineering has been its relatively tight structure of network of cellulose nanofibrils. It has been shown that chondrocytes cells have rather colonized surface of the material than migrating into the network (Svensson, A., Nicklasson, E. Harrah,T., Panilaitis, B., Kaplan, D. Brittberg. M, and Gatenholm, P., Bacterial Cellulose as a Potential Scaffold for Tissue Engineering of Cartilage, *Biomaterials*, 26, 419-431 (2005)). Attempts have been made to promote the migration of smooth muscle cells (SMC) into the BC network by using chemical attractants. SMC were, however only able to enter 10 µm. Recently, a new technology using porogens has been developed to create macroporosity in BC structure (Backdahl, H., Esguerra, M., Delbro, D., Risberg, B., and Gatenholm, P., Engineering microporosity in bacterial cellulose scaffolds, *Journal of Tissue Engineering and Regenerative Medicine*, 2 (6), 320-330 (2008)).

This technique resulted in the preparation of macroporous structures which was found to support smooth muscle cells (Backdahl, H., Esguerra, M., Delbro, D., Risberg, B., and Gatenholm, P., Engineering microporosity in bacterial cellulose scaffolds, Journal of Tissue Engineering and Regenerative Medicine, 2 (6), 320-330 (2008)). The process of preparation of macroporous BC is however based on several steps which include preparation of wax porogen particles, fusing particles and fermentation process with porogens. Using this process, only thin macroporous membranes have been produced. Although the macroporous BC showed promising properties, the manufacturing process is not possible to use for mass production.

The synthesis of nano-cellulose by bacteria such as *Acetobacter xylinum* is taking place between the outer and cytoplasma membrane. Cellulose is a product of carbon metabolism and, depending on the physiological state of the cell, involves either the pentose phosphate cycle or the Krebs cycle coupled with glucogenesis. The growing glucan chains aggregate and are exported through catalytic sites that are linearly arranged on each cell. Bacteria assemble glucan chains into microfibrils and subsequently into a ribbon configuration. In the normal static conditions bacteria will form a pellicle (flake) at the surface of the culture medium. This pellicle will grow in thickness slightly but the thickness is limited by the supply of oxygen and nutrients to the bacteria. Shaped cellulose with limited thickness has been produced in the method using a tubular bioreactor as described in WO2001061026. The oxygen delivery through the silicon support has been explored for manufacturing of tubes for applications such as vascular grafts, as described in EP2079845 and WO2008040729 A2. These structures were however very thin (less than 3 mm thick).

Fermentation conditions play a major role in the determination of material properties of Biosynthetic Cellulose. Use of fermentors and bioreactors has only very limited success due to bacteria sensitivity to agitation and their ability to switch off cellulose production.

In conclusion, the successful use of Biosynthetic Cellulose as implant and scaffold for tissue engineering and regenerative medicine requires a new innovative biofabrication process by which the 3-D shape larger and robust structures, morphology, biomechanical properties and porosity could be controlled in great detail. Such process is described in this patent application and is called 3-D Bioprinting.

SUMMARY OF THE INVENTION

We have invented a novel method to grow BC with a thickness which is theoretically unlimited and in any shape and robust structure. In our novel setup we used a specially designed microfluidic medium administration system to gradually (e.g., continuously) increase the level of culture media. The bacteria continue to produce a BC network when the media level is increased at the rate which is matching the cellulose production. We found that it is possible to optimize the thickness and strength of the resulting BC network by varying the rate and volume of media added. We have developed a microfluidic administration system in which media is added continuously at the air/bacteria interface with a minimum disturbance of bacteria. We have invented a porous mold system in which media diffuse gradually into the mold which results in production of 3D BC structure of predetermined shape and robust structure. We have also invented method to introduce porosity by "printing" a porogen template with controlled porosity which is inserted into 3D BC culture. This invention enables the production of three dimensional structures of biosynthetic cellulose with controlled shape and porosity. Such materials have great potential for applications as implants and scaffolds for tissue engineering and regenerative medicine.

Embodiments of the invention include three-dimensional (3-D) nano-cellulose based structures comprising: a network of multiple layers of biosynthetic cellulose forming a 3-D structure; wherein the network is fabricated in a non-mechanical manner; and wherein the 3-D structure has a density or tensile strength higher than similar structures formed from static-culture techniques or mechanical processes.

Such 3-D nano-cellulose based structures can be prepared with a target 3-D shape, thickness, and strength such as tensile strength. Further, such 3-D cellulose-based structures can be operably configured to be capable of supporting growth of cellular material.

Preferred 3-D nano-cellulose based structures prepared according to embodiments of the present invention are prepared from biosynthetic cellulose originating from *Acetobacter xylinum*, such as the bacterial subspecies *sucrofermentas*.

Cellulose-based structures according to embodiments of the invention can be used as implants or scaffolds for supporting cell growth.

Methods of and systems for preparing such nano-cellulose based structures are also within the scope of the invention. For example, methods of the invention include a method of producing 3-D nano-cellulose based structures comprising: providing bacteria capable of producing cellulose; providing media capable of sustaining the bacteria for the production of nano-cellulose; controlling microbial production rate by administering media with a microfluidic device, for a sufficient amount of time, and under conditions sufficient for the bacteria to produce nano-cellulose at a desired rate; and continuing the administering of the media until a target 3-D structure with a target thickness and target strength is formed which has a morphology defined by a network of multiple layers of interconnected biosynthetic cellulose.

The administering of the media in methods according to embodiments of the invention can involve controlling flow rate and volume of the media using a microfluidic device.

Additionally, microporous molds can be introduced into the systems and methods of the invention as templates for forming the target 3-D nano-cellulose based structures. One manner in which this can be performed includes providing the porous mold by submerging the mold in a bioreactor for growth of the target 3-D structure.

Even further, such methods and systems can comprise means for introducing porosity to the target 3-D structure with porogens added in a computer-controlled manner. More particularly, for example, the porogens can be alginate or wax particles capable of being removed following biofabrication of the 3-D structure.

The methods, systems, and structures of embodiments of the invention can further comprise seeding the three-dimensional nano-cellulose based structure with cells. Use of such 3-D structures includes uses for tissue regeneration, stem cell differentiation, implant or biomedical devices to name a few.

Each of the references cited in this specification is hereby incorporated by reference herein in its entirety.

BRIEF DESCRIPTION OF THE DRAWINGS

FIG. 1 is a schematic diagram illustrating a representative layout for an experimental set up in which a microfluidic media administration system comprising a syringe pump adds a small amount of media to a porous floating ring, which slowly diffuses media into continuously growing cellulose, which grows at the air liquid interface, thereby forming a new layer of cellulose inside the floating ring.

FIGS. 2A and 2B are, respectively, photographs of a BC structure produced by traditional static culture (a gel-like structure) and a more robust BC structure produced by 3-D Bioprinting in accordance with embodiments of the invention.

FIGS. 5A and 5B, respectively, are SEM images showing the differences in network density of the samples represented in FIGS. 3A and 3B, in which the nano-cellulose network sample produced with 3-D Bioprinting process (FIG. 5B) has higher density compared with the sample produced by static culture (FIG. 5A).

FIG. 6 is a schematic illustration showing an exemplary set up that can be used to produce a meniscus implant in accordance with embodiments of the invention, in which a porous meniscus mold is surrounded by culture media, which diffuses into the meniscus mold and allows bacteria inside the mold to grow cellulose at the rate controlled by the rate of media addition.

FIG. 7A is a photograph showing an exemplary printed alginate structure in bacteria culture.

FIG. 7B is a photograph showing the alginate piece of FIG. 7A with two holes and the BC network that has two bumps on it where the holes have been.

FIG. 8 is a photograph showing a representative printer set up for 3-D bioprinting of porous alginate templates.

in FIG. 9B, removal of the sponge and filter, and addition of $CaCl_2$ to the cartridge; and in FIG. 9C, a nozzle diameter of about 25 micron.

DETAILED DESCRIPTION OF VARIOUS EMBODIMENTS OF THE INVENTION

Figure 3A:
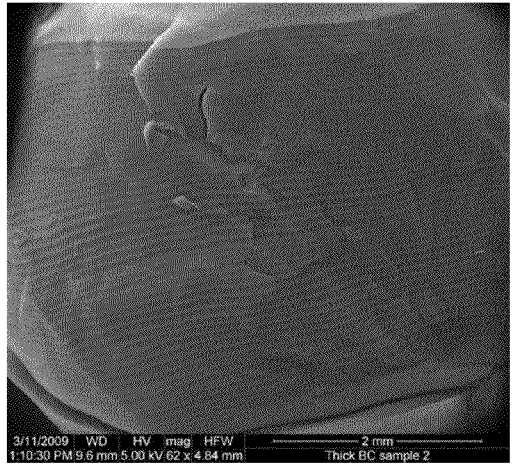
FIGS. 3A and 3B, respectively, are Scanning Electron Microscopy (SEM) images of a sample prepared with traditional static culture and sample produced with a 3D Bioprinting process.

We have invented a novel method to grow BC with a thickness which is theoretically unlimited. In our novel setup we used a specially designed microfluidic medium administration system to gradually (e.g., continuously) increase the level of culture media. The bacteria continue to produce a BC network when the media level is increased at the rate which is matching the nano-cellulose production. We found that it is possible to optimize the thickness and strength of the resulting BC network by varying the rate and volume of media added. In contrast, in static culture there is a limit of thickness of the sample which can be produced. Methods, systems, and structures described herein build upon prior techniques of others including those described in US Published Application Nos. 2002/0182241; 2002/0143403; 2004/0096509; and 2001/0043949; and U.S. Pat. Nos. 6,143,293; 6,197,575; and 5,885,829, the disclosures of which are hereby incorporated by reference in their entireties.

By using a lower medium addition rate, more robust structures were made. This gives the bacteria more time to reinforce the structure they are building before more media is added.

Scanning Electron Microscopy (SEM) images showed some explanations to why the pellicles produced at a lower rate differ in robustness. The more robust structure is always presented to the right. The changes in network density were clearly distinguishable at high magnification.

The problem with thickness was solved, by varying the culture time and conditions the thickness and robustness of the resulting BC network can be controlled.

By using porous molds placed in the bioreactor, which is equipped with medium administration control, we were able to produce large 3D BC robust structures with an exact predetermined shape. We have also invented a method to introduce porosity by "printing" an alginate template with controlled porosity which is inserted into the 3D BC culture. This invention enables the production of three dimensional structures of biosynthetic cellulose with controlled shape and porosity. Such materials have emerging applications as implants and scaffolds for tissue engineering.

Another problem experienced previously was having limited control of the porosity and interconnectivity of the resultant 3D structure. Currently, many techniques are used to create desired pore structures: sintering, salt-leaching, freeze-drying, gas foaming, porogen melting, electro-spinning, and emulsion polymerization to name a few. Regarding BC, paraffin microspheres with porogen melting, and gelatin microspheres, have been used to culture porous BC scaffolds. Unfortunately, all of these fabrication techniques utilize indirect and imprecise control over pore structure. To obtain direct computer control, a modified inkjet printer was developed to fabricate alginate templates for use with a novel BC fermentation technique. Historically, alginates have been used in the food industry as stabilizers, emulsifiers, and gelling agents. Recently, alginate and inkjet printing technology have been combined as a potential means for printing cells and scaffolds. Here, we looked at the potential for alginate bioprinting to be used as a mold for bacterial cellulose and after removal of alginate the pores are hosting mammalian cells.

Representative 3D Bioprinting processes, systems, and devices of embodiments of the invention can employ one or more of the following:

(1) Cells capable of synthesizing one or more extracellular biopolymers.

(2) Culture media capable of maintaining cells under conditions conducive to the bioproduction of one or more extracellular polymers of interest and capable of administration by way of a microfluidic system.

(3) Means for controlling the rate and volume of media administration.

(4) A container or device for containing cells and administered media, in a manner that allows for administration of additional media in a controlled manner.

Such systems can also comprise one or more customizable form to produce desired and/or predetermined 3D geometry. Even further, such systems can comprise means for or be connected with a device for adding porogens in controlled manner for introducing porosity to the 3D structure.

CELLS: The extracellular biopolymers that are synthesized or produced by the cells according to embodiments of the invention include but are not limited to cellulose. Indeed, any biopolymer can be used to prepare 3D structures according to embodiments of the invention depending on a particular application and the qualities and/or properties desired of the resultant 3D structure. For example, polymers that can be used in accordance with embodiments of the invention can also include those identified in International Publication No. WO 2006/042287, which is hereby incorporated by reference in its entirety. In some embodiments, the cells have a native or natural capacity to produce these materials. In other embodiments, the cells can be genetically modified to produce one or more biopolymers, or to alter the properties of the biopolymer (e.g. the composition, tensile strength, dimensions, crystallinity, moisture sorption, electrical properties, magnetic properties, acoustic properties, etc.) or the capacity of the cell to produce the biopolymer may be altered (e.g. to produce larger quantities, or to use diverse energy sources or substrates to produce the biopolymer, or to produce the biopolymer in response to cues such as changes in temperature, pH, media composition, oxygen concentration, light, pressure, electromagnetic field, etc.)

Preferred cellulose producing bacteria may include *Acetobacter, Agrobacterium, Rhizobium, Pseudomonas* or *Alcaligenes* and most preferably species of *Acetobacter xylinum* or *Acetobacter pasteurianus*. The most preferred strain is *Acetobacter xylinum* subspecies *sucrofermentas* BPR2001, trade number 700178™, from the ATCC. In addition, the cells may be genetically engineered to control other useful properties, including but not limited to their charge; the ability to produce a biopolymer if they do not naturally do so; the ability to produce more than one biopolymer, e.g. to produce one or more biopolymers in addition to those that they naturally produce.

MEDIUM: The medium in which the cells are maintained during biopolymer production may be any of many suitable types. The medium is generally liquid. The viscosity of the medium may be altered to produce desired speeds of movement or patterns of distribution of the cells. Further, in some embodiments, the medium may be a gel. In gel-based media embodiments, however, the movement of the cells may be somewhat curtailed. Deposition of polymers in gels may produce more tightly packed polymer formations.

Those of skill in the art are generally familiar with the culture of cells in liquid suspension. Such cultures are usually aqueous, and contain various nutrients and supplements that permit growth and/or maintenance and metabolic activity of the cells, and are suitably oxygenated or not, depending on the requirements of the cells. The nutritive components of the medium may be used by the cell for general metabolic and catabolic activities, as well as to build the biopolymer(s) of interest. Further, the medium may be supplemented in particular to support biopolymer synthesis (e.g. by providing an abundant source of e.g. monomeric polymer building blocks, or to bias the cellular metabolism in favor of biopolymer synthesis, etc.). Examples of suitable media for growing bacteria include but are not limited to: Schramm-Hestrin-medium which contains, per liter distilled water, 20 g of glucose, 5 g of bactopeptone, 5 g of yeast extract, 3.4 g of disodiumhydrogenphosphate dehydrate and 1.15 g of citric acid monohydrate and which exhibits a pH value between 6.0 and 6.3; 0.3 wt % green tea powder and 5w t% sucrose with pH adjusted to 4.5 with acetic acid; Medium composed of (fructose [4% w/v], yeast extract [0.5% w/v], $(NH_4)_2SO_4$ [0.33% w/v], $KH_2PO_4$ [0.1w/v], $MgSO_4.7H2O$ [0.025% w/v], corn steep liquor [2% v/v], trace metal solution [1% v/v, (30 mg EDTA, 14.7 mg $CaCl_2.2H_2O$, 3.6 mg $FeSO_4.7H_2O$, 2.42 mg $Na_2MoO_4.2H_2O$, 1.73 mg $ZnSO_4.7H_2O$, 1.39 mg $MnSO_4.5H2O$ and 0.05 mg $CuSO_4.5H_2O$ in 1 liter distilled water)] and vitamin solution [1% v/v (2 mg inositol, 0.4 mg pyridoxine HCl, 0.4 mg niacin, 0.4 mg thiamine HCl, 0.2 mg para-aminobenzoic acid, 0.2 mg D-panthothenic acid calcium, 0.2 mg riboflavin, 0.0002 mg folic acid and 0.0002 mg D-biotin in 1 liter distilled water)]). Any medium comprised of sugar source, nitrogen source and vitamins can be successful used. Bacteria grow even in apple or pineapple juice, coconut milk, beer waste, or wine.

The media may be altered to include ions such that ions are deposited onto the biopolymer. This can include but are not limited to: Schramm-Hestrin-medium with 1, 5, or 10% PBS (Phosphate Buffered Saline), Schramm-Hestrin-medium with 1%, 5%, or 10% 0.1 molar calcium chloride, or any suitable culture media with an increased concentration of one or more ions, including but not limited to potassium, calcium, phosphate, or sodium. The media can also contain sodium alginate. The media described herein are provided for exemplary purposes and are not intended to be limiting. Any of the components of the media can be omitted and/or the media can comprise additional components to achieve a desired result. The media capable of use in embodiments of the invention are easily created by those skilled in the art.

Example 1

Production of Robust 3D BC Structure with Potentially Unlimited Thickness

For controlled 3D Biosynthetic Cellulose structure to grow, a medium administration system has been designed, which is shown schematically in FIG. 1. More particularly, in this embodiment, FIG. 1 provides a representative layout for an experimental set up in which a microfluidic media administration system comprising a syringe pump adds a small amount of media to a porous floating ring, which slowly diffuses media into continuously growing cellulose, which grows at the air liquid interface, thereby forming a new layer of cellulose inside the floating ring.

Any means for administering the media can be used. Preferably, administration systems capable of controlling the rate and/or volume of media addition are highly desired. The system was composed of syringe pump, 100 ml sterile syringe and sterile silicone tubing. 100 ml of medium composed of (fructose [4% w/vl], yeast extract [0.5% w/v], (NH4)2SO4 [0.33% w/v], KH2PO4 [0.1% w/v], MgSO4.7H2O [0.025% w/v], corn steep liquor [2% v/v], trace metal solution [1% v/v, (30 mg EDTA, 14.7 mg CaCl2.2H2O, 3.6 mg FeSO4.7H2O, 2.42 mg Na2MoO4.2H2O, 1.73 mg ZnSO4.7H2O, 1.39 mg MnSO4.5H2O and 0.05 mg CuSO4.5H2O in 1 liter distilled water)] and vitamin solution [1% v/v (2 mg inositol, 0.4 mg pyridoxine HCl, 0.4 mg niacin, 0.4 mg thiamine HCl, 0.2 mg para-aminobenzoic acid, 0.2 mg D-panthothenic acid calcium, 0.2 mg riboflavin, 0.0002 mg folic acid and 0.0002 mg D-biotin in 1 liter distilled water)]) was sterilized by microfiltration and placed in the sterile syringe. 5 ml of *Acetobacter xylinum* subsp. *sucrofermentas* BPR2001, trade number 700178™, from the ATCC bacteria suspension taken from preculture was added into 100 ml sterilized glass container (the bottom of container has to be completely covered by bacteria suspension). The bacteria suspension in the beaker was placed in incubator holding 30 degree Celsius for 2-24 hours. The time can be varied between 2 hours and 24 hours until confluent layer of Biosynthetic Cellulose, BC is produced. At that time the medium is started to be added using syringe pump at such a low rate that it matches the production rate of cellulose. It is preferential to keep the temperature of medium at 30 degree C. The good indication that the addition rate matches the consumption rate is that no free medium is seen in the beaker. BC layers form most readily at the intersection of the solid, liquid, air boundary.

The layers continue to develop across the remaining liquid-air boundary and remain attached to the outside solid boundary anchor points. It has also been observed that thin BC layers are neutrally buoyant, even when the layer is detached from its initial anchor points. When culture media is added above an existing BC layer, growth at that layer is impeded and cellulose production resumes at the new solid-liquid-air interface. When medium is added dropwise above the growing BC pellicle the crater-like defects in the forming structure appears. We have solved that problem in Example 1 using a porous microfluidic floating ring device made of Teflon (see FIG. 1). Such a device made it possible to distribute medium into growing culture without disturbing growing pellicle. The microfluidic device can be floated or attached to z stage and moved vertically with a rate which is matching fluid addition rate and Biosynthetic Cellulose production rate. The device designed and used in Example 1 was able to accommodate the growth of multiple BC scaffold layers. The thickness of produced BC material was unlimited in this example, however, the process in this example was stopped when the beaker was filled with BC.

The morphology of the produced sample can be seen in FIG. 2B. It is a robust structure compared with gel-like structure, which was prepared in traditional static culture (FIG. 2A), in which all the medium was added from the beginning and bacteria suspension was added to the medium. In such static culture it took very long time to grow thick structures due to medium diffusion problems. The structures of BC produced by 3D Bioprinting and BC produced by static culture were compared with regards to morphology using Scanning Electron Microscopy (SEM). SEM images (FIGS. 2A-B, 3A-B, and 4A-B) showed some explanations as to why the pellicles produced at lower rate differ in robustness.

Figure 3B:
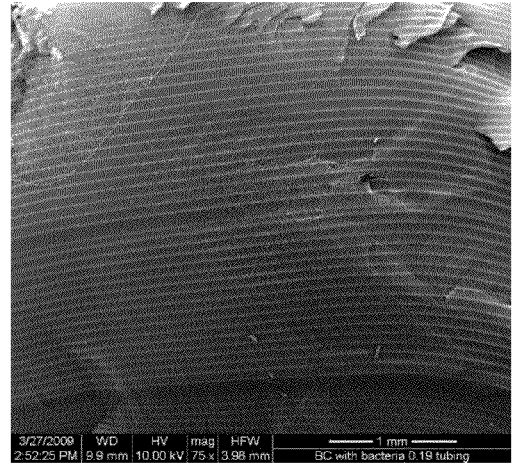

As shown in FIGS. 3A-B, at low magnification, the striped regions are more distinct in the cross sections of the samples.

Figure 4A:
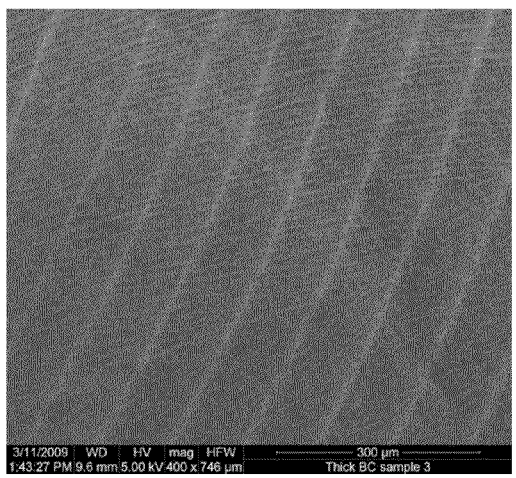
FIGS. 4A and 4B, respectively, are SEM images of the samples represented in FIGS. 3A and 3B, at higher magnification, showing a more dense nano-cellulose network in the more robust structure produced by 3-D Bioprinting (FIG. 4B).
Figure 4B:
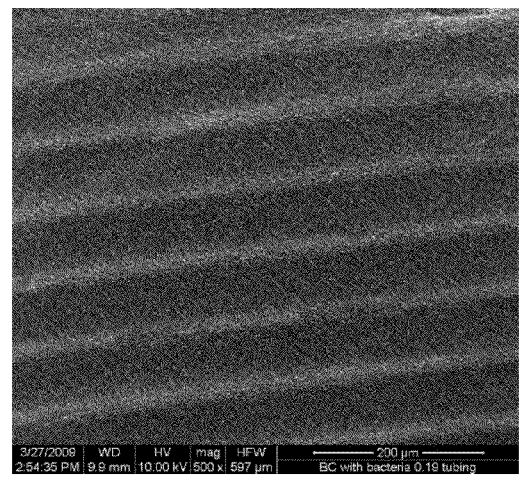

The changes in network density were clearly distinguishable at high magnification. For example, as shown in FIG. 4, at higher magnification an orientation is seen between the layers in both samples. The nano-cellulose network is however denser in the more robust structure produced by 3-D Bioprinting (FIG. 4B).

As shown in FIGS. 5A-B, close up images of the samples show differences in network density. More particularly, the nano-cellulose network has a higher density in the sample produced with 3-D Bioprinting process (FIG. 5B) compared with the static-culture produced sample (FIG. 5A). White structures in the right picture are the bacteria, which were not removed before taking the pictures in that sample.

TABLE 1

Mechanical Properties of Biosynthetic Cellulose Structures

| Material | Tensile Strength (MPa) | Strain (%) | Modulus (MPa) |
|---|---|---|---|
| 3D Bioprinted BC | 1.05 | 62 | 2.50 |
| Static Culture | 0.39 | 57 | 0.80 |

As shown in the examples described in this specification, the biosynthetic cellulose structures prepared in accordance with embodiments of the invention can have a tensile strength and/or a modulus of elasticity of about one, two, three or more times that of similar structures prepared by way of traditional static culture techniques. Although biosynthetic cellulose structures can be prepared having any desired mechanical properties, preferred are such structures having any improvement in tensile strength, strain, and/or a modulus of elasticity as compared with traditional static-culture prepared structures. Preferred are 3-D cellulose-based structures having a tensile strength ranging from above 0 to about 5 MPa. For example, the tensile strength of scaffold embodiments according to the invention can range from about 0.2 to about 4 MPa, or from about 0.4 to about 3 MPa, or from about 0.5 to about 2 MPa, or from about 0.6 to about 1.5 MPa, or from about 0.7 to about 1 MPa, or from about 0.8 to about 1.2 MPa, and so on. Preferred structures can have a modulus of elasticity ranging from above 0 to about 10 MPa, such as from about 0.3 to about 8 MPa, or from about 0.5 to about 5 MPa, or from about 0.75 to about 4 MPa, or from about 0.8 to about 3 MPa, or from above about 0.8 to about 2.75 MPa, or from about 1 to about 2 MPa, and so on. Strain measurements of the materials in accordance with embodiments of the invention can range, for example, from about 30% to about 90% or higher, such as from about 45% to about 75%, or from about 60% to about 70%.

For example, the biosynthetic cellulose structures of embodiments of the invention can preferably have a 3-D interconnected microfibril network joined together by way of hydrogen bonding to exhibit high tensile strength. The degree of polymerization can also be controlled in preparing such structures to obtain a target strength resultant material.

Example 2

Production of Multilayer BC Structures with Variation of Properties in Various Layers The thickness of the 3D structure produced in experimental set up shown in FIG. 1 and with details described in Example 1 has been modified by addition from the second syringe pump sterilized distilled water. That stopped the cellulose growth. Upon completion of the first BC scaffold layer, an additional 0.025 mL of culture media was added on the top of the surface covering the existing layer. Bacteria suspension taken from preculture was added on the top of the pellicle and the new a pellicle was grown at the liquid-air-interface. This process was repeated. Since we found that the medium addition rate affected morphology and robustness of each layer we have performed experiments with varying medium addition rate. We were able to produce multilayer structures with variation of morphology and mechanical properties. This is of great importance when the BC material is used as implant and the different material properties are required in different layers (for example meniscus, ear, nose, bone grafts, and liver to name a few).

Example 3

Production of large 3D BC Robust Structures with Exact Predetermined Shape

Using the experimental set up as described in Example 1 and displayed in FIG. 1, large 3D BC robust structures can be prepared. The system was composed of syringe pump, 100 ml sterile syringe and sterile silicone tubing. 100 ml of medium composed of (fructose [4% w/vl], yeast extract [0.5% w/v], $(NH_4)_2SO_4$ [0.33% w/v], $KH_2PO_4$ [0.1% w/v], $MgSO_4.7H_2O$ [0.025% w/v], corn steep liquor [2% v/v], trace metal solution [1% v/v, (30 mg EDTA, 14.7 mg $CaCl_2.2H_2O$, 3.6 mg $FeSO_4.7H_2O$, 2.42 mg $Na_2MoO_4.2H_2O$, 1.73 mg $ZnSO_4.7H_2O$, 1.39 mg $MnSO_4.5H_2O$ and 0.05 mg $CuSO_4.5H_2O$ in 1 liter distilled water)] and vitamin solution [1% v/v (2 mg inositol, 0.4 mg pyridoxine HCl, 0.4 mg niacin, 0.4 mg thiamine HCl, 0.2 mg para-aminobenzoic acid, 0.2 mg D-panthothenic acid calcium, 0.2 mg riboflavin, 0.0002 mg folic acid and 0.0002 mg D-biotin in 1 liter distilled water)]) was sterilized by microfiltration and placed in the sterile syringe. In order to produce BC in an exact (desired or predetermined) shape we use the porous mold which we placed in the beaker (FIG. 6). As shown in FIG. 6, the porous meniscus is surrounded by media, which diffuses into meniscus and allows bacteria inside to grow cellulose.

In Example 3 we used a meniscus form to produce a customizable BC meniscus implant using the precise desired shape of a patient's injured meniscus. The MRI picture was taken on the patient's knee and the image was converted into slices and the computer model was created. The hard copy of the target meniscus was produced by 3D printer using a sintering method. The replica of the meniscus shape was produced by casting silicon with salt particles. After curing, the mold was washed with water and salt porogen particles were removed from the mold. This process resulted in the formation of a porous mold with the exact target shape of the patient's meniscus. The porous mold was placed on the bottom of the beaker and seeded with 2 ml of bacteria suspension taken from bacteria preculture. After 2-24 hours, when a confluent layer of BC was produced in the meniscus form, medium addition began at the rate which was matching BC production in the mold. The medium was diffusing through the porous mold. After 5 days of such culture the robust BC meniscus in exactly the shape of the patient's injured meniscus was produced. The BC meniscus was removed from the mold, washed in 0.1 m NaOH solution at 60 degree Celsius for 48 hours and then washed several days with DI water. After sterilization by autoclaving, the BC meniscus implant was ready for use as implant.

Objects with various sizes can be obtained using embodiments of the invention. For example, it is possible to obtain a 3-D structure for use as an ear implant, which has a very complex geometry and a length, for example, of up to about 5-10 cm. Craniofacial bone grafts are also possible according to embodiments of the invention with sizes of up to about 10×10 cm and a thickness of about 5 mm. Further, for example, disc-shaped breast implants having a diameter of about 5-20 cm and a thickness of up to about 10 cm are also possible according to the invention. Essentially, the size, shape, and strength of the resultant 3-D structures prepared in accordance with the embodiments described in this specification, including modifications within the skill of the art, is limitless. Large, robust, complex 3-D structures, which can be used as implants, are made possible by this invention.

Example 4

Demonstration of the Inclusion of Ducts and Pores into BC Scaffold using Ink Jet Printing of Alginate We have prepared the alginate template by printing 0.1 m calcium chloride FIG. 7A was printed and placed horizontally in the beaker. 5 ml of *Acetobacter xylinum* subsp. *sucrofermentas* BPR2001, trade number 700178™, from the ATCC bacteria suspension taken from preculture was added into 100 ml sterilized glass container (the bottom of the container has to be completely covered by bacteria suspension). The bacteria suspension in the beaker, covering the alginate template was placed in an incubator capable of maintaining a temperature of 30 degrees Celsius for 2-24 hours. The processing time can be varied between 2 hours and 24 hours until a confluent layer of Biosynthetic Cellulose, BC is produced. At that time medium addition can be started using a syringe pump at such a low rate that it matches the production rate of cellulose. It is preferential to keep the temperature of the medium at 30 degree C. The media was then added using a microfluidic medium administration system as described in Example 1 and as shown in FIG. 1. The cellulose was grown and was able to fill the holes in the alginate template. After culturing the template, the bacteria was removed using a 0.1 m NaOH solution. The resulted structure is shown in FIG. 7B.

Example 5

Demonstration of the Inclusion of Pores into the 3D Scaffold using Injected Wax Particles Injection of wax particles prior to growth of BC will result in porous scaffold layers after the particles are melted and removed. Physiological phenomena such as cell invasion, vascularization and nutrient transport as well as mechanical properties are all influenced by the overall geometry and porosity of the system. To mimic the complex porous structure found in the ECM of many tissues, wax particles were introduced into the growing pellicle to impede cellulose production in specific regions.

We have developed a printer setup that allows printing of detailed structures in alginate. A band with two holes in it was printed and put into the BC cultures explained above. An ink jet printer as shown in FIG. 8 was used to inject wax particles. The exemplary set up is based on a Dell 720p, or Lexmark Z600, printer. Our intent was to leave as much of the original control hardware intact as possible and, in effect, fool the printer into thinking it was printing onto a sheet of paper with ink.

Concentrated bacteria suspension was added followed by addition of medium in a manner similar to that described in Example 1. The sample will then be heated and processed to remove the injected wax particles leaving a porous BC scaffold layer.

Example 6

Bioprinting of Porous 3D BC using Alginate

We have prepared the alginate template in situ by printing 0.1 m calcium chloride solution into 1% solution of alginate which was added into the medium. We have also made reverse experiment where we printed alginate into medium containing calcium solution. 5 ml of *Acetobacter xylinum* subsp. *sucrofermentas* BPR2001, trade number 700178™, from the ATCC bacteria suspension taken from preculture was added into 100 ml sterilized glass container (the bottom of container has to be completely covered by bacteria suspension). The bacteria suspension in the beaker, covering the alginate template was placed in incubator holding 30 degree Celsius for 2-24 hours. The time can be varied between 2 hours and 24 hours until confluent layer of Biosynthetic Cellulose, BC is produced. At that time the medium is started to be added using syringe pump at such a low rate that it matches the production rate of cellulose. It is preferential to keep the temperature of medium at 30 degree C. The media was then added using microfluidic medium administration system as described in Example 1 and shown in FIG. 1.

Figures 9A, 9B, 9C:
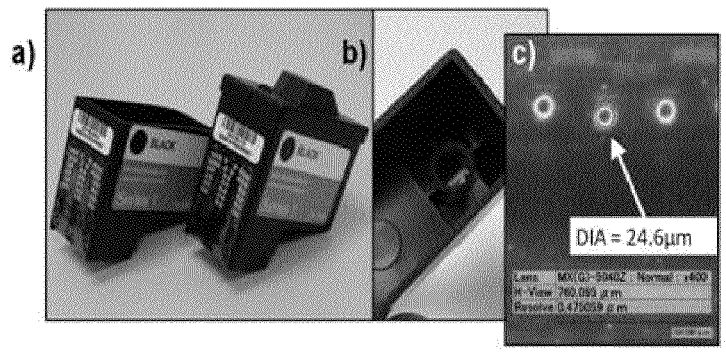
FIGS. 9A-C are photographs showing a representative manner for preparing for 3-D bioprinting, including, in FIG. 9A, removal of the top of the ink-jet cartridge.
Figures 10A, 10B, 10C:
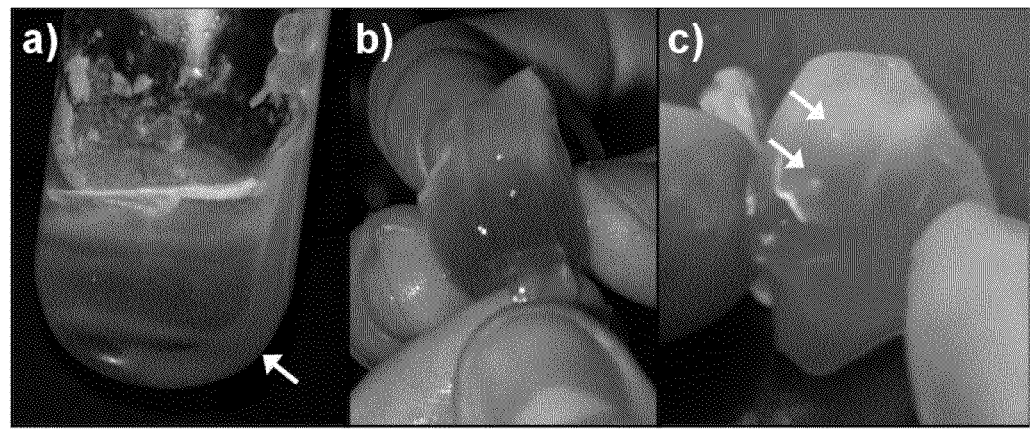
FIGS. 10A-C are photographs showing an example of cultured BC in vertical growth tube with bioprinted alginate template (FIG. 10A); removal of the alginate template from BC (FIG. 10B); and molded columns of alginate in BC culture (FIG. 10C).

We have used a printer as shown in FIG. 8 and ink cartridges as shown in FIGS. 9A-C. More particularly, an exemplary method of ink jet preparation is shown in FIGS. 9A-C: a) the top of the cartridge was removed; b) the sponge and filter were removed and $CaCl_2$ was added to the cartridge; and c) the nozzle diameter is 25 micron. We were able to print the mold and use the alginates as porogens. The resultant structures are shown in FIGS. 10A-C: a) cultured BC in vertical growth tube with bioprinted alginate template; b) removal of alginate template from BC; and c) molded columns of alginate in BC culture.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Further, it will be appreciated that modifications to the above-described embodiments can be made by including elements described in any other embodiment or by using less than or otherwise omitting any detailed feature. The description of the invention provided is merely exemplary in nature and, thus, variations that do not depart from the essence of the invention are intended to be within the scope of the invention.

The invention claimed is:

1. A method of producing 3-D nano-cellulose based structures comprising:
   providing bacteria capable of producing nano-cellulose;
   providing media capable of sustaining the bacteria for the production of nano-cellulose;
   controlling microbial production rate by administering media with a microfluidic device, for a sufficient amount of time, and under conditions sufficient for the bacteria to produce nano-cellulose at a desired rate;
   continuing the administering of the media until a target three-dimensional structure with a target thickness and target strength is formed which has a morphology defined by a network of multiple layers of interconnected biosynthetic cellulose.

2. The method of claim 1, wherein the administering of the media involves controlling flow rate and volume of the media using a microfluidic device.

3. The method of claim 1, further comprising providing a microporous mold as a template for forming the target 3-D nano-cellulose based structure.

4. The method of claim 1 comprising introducing porosity to the target 3-D structure with porogens added in a computer-controlled manner.

5. The method of claim 3, wherein providing the porous mold comprises submerging the mold in a bioreactor for growth of the target 3-D structure.

6. The method of claim 4, wherein the porogens are alginate or wax particles capable of being removed following biofabrication of the 3-D structure.

7. The method of claim 1, further comprising seeding the three-dimensional nano-cellulose based structure with cells.

8. The method of claim 1, wherein the resultant 3-D nano-cellulose-based structure of claim has a tensile strength of about 1 MPa or higher or a modulus of about 2.5 MPa or higher.

* * * * *